(12) United States Patent
Tokura et al.

(10) Patent No.: US 7,994,386 B2
(45) Date of Patent: Aug. 9, 2011

(54) ABSORBENT ARTICLE

(75) Inventors: Yuka Tokura, Kagawa-ken (JP);
Yukihiro Ito, Kagawa-ken (JP);
Toshihisa Hayashi, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 752 days.

(21) Appl. No.: 11/524,109

(22) Filed: Sep. 20, 2006

(65) Prior Publication Data
US 2007/0093773 A1     Apr. 26, 2007

(30) Foreign Application Priority Data

Oct. 24, 2005    (JP) .................................. 2005-309119

(51) Int. Cl.
*A61F 13/15*    (2006.01)
*A61F 13/20*    (2006.01)
(52) U.S. Cl. ......................................... 604/380; 604/379
(58) Field of Classification Search .................. 604/378, 604/382, 380; 428/156, 196
See application file for complete search history.

(56) References Cited

U.S. PATENT DOCUMENTS

| | | | | |
|---|---|---|---|---|
| 5,919,178 | A | * | 7/1999 | Widlund ....................... 604/368 |
| 6,172,276 | B1 | | 1/2001 | Hetzler et al. |
| 2002/0068150 | A1 | * | 6/2002 | Taneichi et al. ............... 428/138 |
| 2002/0103469 | A1 | | 8/2002 | Chen et al. |
| 2003/0084983 | A1 | * | 5/2003 | Rangachari et al. .......... 156/181 |
| 2003/0093047 | A1 | | 5/2003 | Nguyen et al. |
| 2003/0143376 | A1 | * | 7/2003 | Toyoshima et al. ........... 428/156 |

FOREIGN PATENT DOCUMENTS

| | | |
|---|---|---|
| EP | 1 184 021 A2 | 8/2001 |
| EP | 1 209 271 A1 | 10/2001 |
| JP | H04-034082 A | 2/1992 |
| JP | 09-154870 | 6/1997 |
| JP | 2003-024371 A | 1/2003 |
| JP | 2003-250836 | 9/2003 |
| JP | 2003-250836 A | 9/2003 |
| JP | 2004-208833 A | 7/2004 |
| JP | 3611838 B | 10/2004 |
| JP | 2005-185563 | 7/2005 |
| UA | 61104 | 5/1998 |
| UA | 908 U | 7/2001 |
| UA | 2002097627 | 9/2002 |

OTHER PUBLICATIONS

English translation of specification for JP 2003-250836 A (Toyoshima et al).*
English translation of specification of JP 2005-185563 A to Konishi et al.*
English translation of Office Action issued in corresponding Ukrainian Application No. a200805241, mailed Apr. 5, 2010.
European Search report from corresponding European 06797293.5, mailed May 25, 2010, 4 pages.

* cited by examiner

*Primary Examiner* — Melanie J Hand
(74) *Attorney, Agent, or Firm* — Brinks Hofer Gilson & Lione

(57) ABSTRACT

The present invention provides an absorbent article having superior surface characteristics and improved absorbing ability. The absorbent article of the present invention includes a liquid permeable top sheet 10 disposed at a skin-side, a liquid impermeable back sheet 20 disposed at a garment side, and an absorbent body interposed between the top sheet and the back sheet. An apparent thickness (t2) of the top sheet 10 is 70% to 95% to an apparent thickness (t1) of the panty liner 1. The absorbent body 30 consists of a structure, in which a capillary rise height (h2) is higher than a capillary rise height (h1) of the top sheet 10.

9 Claims, 2 Drawing Sheets

ABSORBENT ARTICLE

This application is based on and claims the benefit of priority from Japanese Patent Application No. 2005-309119, filed on 24 Oct. 2005, the content of which is incorporated herein by reference.

BACKGROUND OF THE INVENTION

1. Field of the Invention

The present invention relates to an absorbent article such as a panty liner, a sanitary napkin, and a diaper.

2. Related Art

Conventionally, it is known in the art that absorbent articles such as a panty liner, a sanitary napkin, and a diaper have a structure consisting of a liquid permeable top sheet disposed at a skin-side, a liquid impermeable back sheet disposed at a garment side, and an absorbent body interposed between the top sheet and the back sheet.

In addition, to improve absorbing ability for quickly transferring body fluid into the absorbent body, and surface characteristics, in which the skin contact surface to the wearer is soft to decrease impact to a skin, the materials of the top sheet, the back sheet, and the absorbent body have been studied.

For example, according to the Japanese Patent No. 3611838, the first layer disposed at the skin side, and the second layer disposed at the absorbent body side are laminated. Furthermore, the top sheet, in which the first layer and the second layer are contact in the whole area, and partially joined for the whole area, is disclosed. In this top sheet, the apparent thickness of the first layer is 50% to 80% that of the second layer. In addition, the density of the second layer is higher than that of the first layer.

When the apparent thickness of the first layer is much thinner than that of the second layer, the first layer cannot be sufficiently formed, so that the absorbent article has a harsh texture for the wearer. Alternatively, when the apparent thickness of the first layer is much thicker than that of the second layer, the distance between a skin contact surface and the second layer becomes longer, so that body fluid cannot be quickly transferred into the second layer to make the wearer feel uncomfortable from body fluid remaining at the skin contact surface. Thus, the top sheet as described in the Japanese Patent No. 3611838, in which the apparent thickness of the first layer is at least 50% in regards to that of the second layer to sufficiently form the first layer, has a soft to the touch for the wearer. In addition, the top sheet, in which the apparent thickness of the first layer is no more than 80% of that of the second layer, can take body fluid in the second layer by way of capillary action. Furthermore, the top sheet, in which the density of the second layer is higher than that of the first layer, can quickly transfer body fluid in the second layer.

Thus, when the top sheet described in the Japanese Patent No. 3611838 is applied to an absorbent article, superior surface characteristics can be obtained; however, the structure of the absorbent body is not limited, in particular. The absorbent article cannot enhance to transfer body fluid transferred in the second layer into the absorbent body, and inhibit reversing body fluid transferred in the absorbent body toward the skin side, so that superior absorbing ability cannot be obtained.

Therefore, the objective of the present invention is to provide an absorbent article having superior surface characteristics and improved absorbing ability.

SUMMARY OF THE INVENTION

The inventor provides an absorbent article described below.

According to a first aspect of the present invention, an absorbent article includes a liquid permeable top sheet, a liquid impermeable back sheet, an absorbent body interlaced between the top sheet and the back sheet, in which the apparent thickness (t2) of the top sheet is 70% to 95% to the apparent thickness (t1) of the absorbent article, and the capillary rise height (h2) of the absorbent body is higher than the capillary rise height (h1) of the top sheet.

When t2 of the top sheet disposed at the skin side of a wearer is much smaller than t1 of the absorbent article, the distance between the skin contact surface and the absorbent body becomes smaller, so that the moisture of the skin contact surface increases because of the absorbent body which has absorbed body fluid. In addition, because the top sheet is not formed well enough to reduce or disperse the pressure from the wearer to the absorbent body, body fluid absorbed in the absorbent body is reversed toward the skin side. Thus, according to the first aspect of the present invention, t2 is at least 70% to that of t1. Therefore, the skin contact surface and the absorbent body are sufficiently segregated, so that increased moisture at the skin contact surface caused by the absorbent body which has absorbed body fluid is inhibited. In addition, because the top sheet has been formed well enough so as to reduce or disperse the pressure from the wearer to the absorbent body, reversal of body fluid absorbed in the absorbent body toward the skin side can be controlled.

When t2 of the absorbent body is much smaller than t1 of the top sheet, the member other than the top sheet, such as the back sheet disposed at the absorbent body or the garment side of the wearer, cannot be sufficiently provided, so that the absorption of the body fluid, the concealing characteristics toward the garment side, and the like may be insufficient. Thus, according to the first aspect of the present invention, t2 is no more than 95% to that of t2. Therefore, the absorbent body, the back sheet, and the like can be provided well enough to sufficiently absorb body fluid and to inhibit body fluid seepage into the garment side.

The capillary rise height (h2) of the absorbent body is higher than the capillary rise height (h1) of the top sheet. Therefore, body fluid, which is discharged to the top sheet, is absorbed into the absorbent body side, to control body fluid remaining at the skin contact surface, which causes discomfort for the wearer. In addition, since body fluid which was drawn into the absorbent body is held inside the absorbent body, more body fluid can be absorbed and held.

Therefore, the absorbent article described in the first aspect of the invention has superior surface characteristics and absorbing ability.

According to a second aspect of the absorbent article as described in the first aspect of the present invention, the apparent thickness (t1) is from 0.5 mm to 5 mm.

When the apparent thickness (t1) is too small, the components, such as the top sheet, the absorbent, and the back sheet cannot be provided well enough to sufficiently absorb body fluid. Alternatively, when t1 is too large, the wearer feels great discomfort. Thus, the apparent thickness (t1) of the absorbent article according to the second aspect of the present invention is 0.5 mm or more, so that these components can be provided well enough to sufficiently absorb body fluid, which means the absorbing ability, is superior. In addition, t1 is 5 mm or less, the feelings of discomfort is reduced for the wearer. Thus, the absorbent article described in the second aspect of the present invention can be applied to a thinner absorbent article, such as a panty liner.

According to a third aspect of the absorbent article as described in the first aspect of the present invention, the top sheet provides a plurality of concave portions.

According to the third aspect of the present invention, the top sheet provides a plurality of concave portions. Thus, through the portion of the skin surface of the top sheet in contact with the absorbent body, body fluid discharged is quickly transferred into the absorbent body to control body fluid remaining at the skin contact surface, which causes discomfort for the wearer. Therefore, the absorbent article described in the first aspect of the invention has superior surface characteristics and absorbing ability.

According to a fourth aspect of the absorbent article as described in the third aspect of the present invention, the depth of the concave portion is from 50% to 95% the apparent thickness of the top sheet.

When the depth of the concave portion is too small in regards to the apparent thickness (t2) of the top sheet, the distance between the skin contact surface and absorbent body is not sufficiently reduced, and the discharged body fluid may not be quickly transferred into the absorbent body. Thus, according to the fourth aspect of the present invention, the depth of the concave portion is at least 50% to that of t2, so that the skin side of the top sheet and the absorbent body become closer in the region at which these concave portions are provided. Therefore, through the region, discharged body fluid is quickly transferred into the absorbent body, to quickly control body fluid remaining at the skin contact surface, which causes discomfort for the wearer.

Alternatively, when the concave portion is too deep to t2, the thickness of the region where the concave portions are provided is small, so that body fluid absorbed in the absorbent body is reversed toward the skin side through the region. Thus, according to the fourth aspect of the present invention, the depth of the concave portion is no more than 95% to that of t2. The region, at which the concave portions are provided, is sufficiently formed. Thus, through the region, body fluid absorbed in the absorbent body reversed toward the skin side through the region can be controlled.

Therefore, the absorbent article described in the fourth aspect of the present invention has superior surface characteristics and absorbing ability.

According to a fifth aspect of the absorbent article as described in the third aspect of the present invention, the concave portions are formed of the embossed compressed portions.

According to the fifth aspect of the present invention, the concave portions are formed of the embossed compressed portions, so that a relatively high density region is formed at the region of the top sheet, in which the embossed compressed potions are disposed. Discharged body fluid is absorbed into the region, which is a high density region, by way of capillary action based on a density gradient. Thus, the body fluid is quickly transferred into the absorbent body to quickly control the body fluid remaining at the skin contact surface, which causes discomfort for the wearer. Therefore, the absorbent article described in the fifth aspect of the invention has superior surface characteristics and absorbing ability.

According to a sixth aspect of the absorbent article as described in the first aspect of the present invention, the absorbent body includes fiber on which hydrophilic oil is applied.

According to the sixth aspect of the absorbent body, the absorbent body includes fiber on which hydrophilic oil is applied. The degree of hydrophilicity of the absorbent body can be relatively higher than that of the top sheet. Thus, body fluid is quickly transferred into the absorbent body, to quickly control the body fluid remaining at the skin contact surface, which causes discomfort for the wearer. Therefore, the absorbent article described in the sixth aspect of the invention has superior surface characteristics and absorbing ability.

According to a seventh aspect of the absorbent article as described in the first aspect of the present invention includes cellulosic fiber.

According to the seventh aspect of the present invention, the absorbent body includes cellulosic fiber to increase its hydrophilicity relatively higher than the hydrophilicity of the top sheet. Thus, body fluid is quickly transferred into the absorbent body, to quickly control body fluid remaining at the skin contact surface, which causes discomfort for the wearer. Therefore, the absorbent article described in the seventh aspect of the invention has superior surface characteristics and absorbing ability.

According to an eighth aspect of the absorbent article of the present invention, the density of the absorbent is higher than that of the top sheet.

According to the eighth aspect of the present invention, the density of the absorbent body is higher than that of the top sheet, so that discharged body fluid is absorbed into the absorbent body, by way of capillary action based on a density gradient. Thus, body fluid is quickly transferred into the absorbent body, to quickly control body fluid remaining at the skin contact surface, which causes discomfort for the wearer. Therefore, the absorbent article described in the eighth aspect of the invention has superior surface characteristics and absorbing ability.

According to a ninth aspect of the absorbent article as described in the eighth aspect of the present invention, the density of the absorbent body is from $0.05 \text{ g/cm}^3$ to $0.25 \text{ g/cm}^3$.

According to the ninth aspect of the present invention, the density of the absorbent body is $0.05 \text{ g/cm}^3$ or more, so that the density of the absorbent body is higher than that of the density of the top sheet. Thus, body fluid is quickly transferred into the absorbent body, to quickly control body fluid remaining at the skin contact surface, which causes discomfort for the wearer. Alternatively, the density of the absorbent body is $0.25 \text{ g/cm}^3$ or less, so as to absorb and maintain more body fluid. Therefore, the absorbent article described in the ninth aspect of the invention has superior surface characteristics and absorbing ability.

According to a tenth aspect of the absorbent article as described in the eighth aspect of the present invention, the density of the top sheet is from $0.0125 \text{ g/cm}^3$ to $0.150 \text{ g/cm}^3$.

According to the tenth aspect of the present invention, the density of the top sheet is $0.0125 \text{ g/cm}^3$ or more to sufficiently form the top sheet, so that the absorbent article has a soft touch for the wearer. Alternatively, the density of the top sheet is $0.150 \text{ g/cm}^3$ or less, so that body fluid is absorbent into the top sheet, to quickly control body fluid remaining at the skin contact surface, which causes discomfort for the wearer. Therefore, the absorbent article described in the tenth aspect of the invention has superior surface characteristics and absorbing ability.

According to the absorbent article of the present invention, the following advantageous effect is provided. The apparent thickness (t2) of the top sheet is no less than 70% to that of the apparent thickness (t1) of the absorbent article. Therefore, the skin contact surface and the absorbent body are sufficiently separated, so that the increase of moisture at the skin contact surface caused by the absorbent body which has absorbed body fluid is restricted. In addition, the top sheet is provided well enough to reduce or disperse the pressure from the wearer to absorbent body, reversing body fluid absorbed in the absorbent body toward the skin side can be controlled.

Thus, t2 is no more than 95% to that of t2. Therefore, the absorbent body, the back sheet, and the like can be provided well enough to sufficiently absorb body fluid and to prevent the movement of body fluid into the garment side.

The capillary rise height (h2) of the absorbent body is higher than the capillary rise height (h1) of the top sheet.

Therefore, body fluid, which is discharged to the top sheet, is absorbed into the absorbent body side, to control body fluid remaining at the skin contact surface, which causes discomfort for the wearer. In addition, since body fluid which was drawn into the absorbent body is held inside the absorbent body, more body fluid can be absorbed and held.

DETAILED DESCRIPTION OF THE INVENTION

One embodiment of the present invention is described based on the figures.

Whole Configuration of the Absorbent Article

Figure 1:
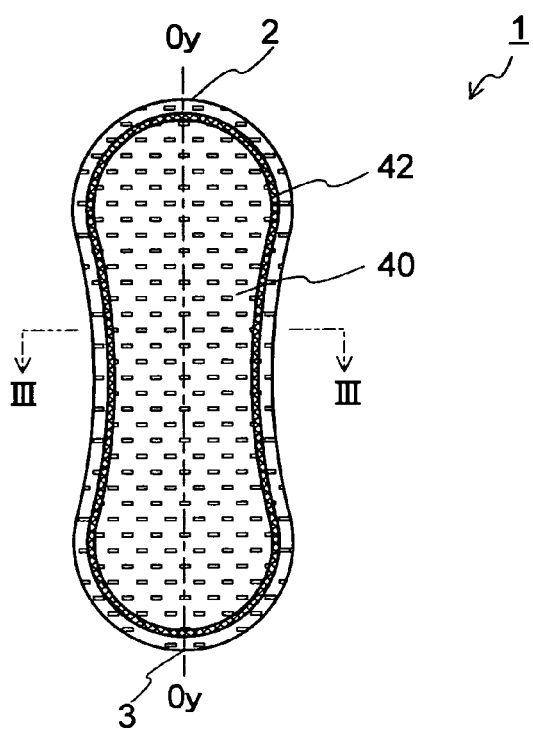
FIG. 1 shows the plan view to illustrate the skin side surface of the absorbent article according to one embodiment of the present invention.
Figure 2:
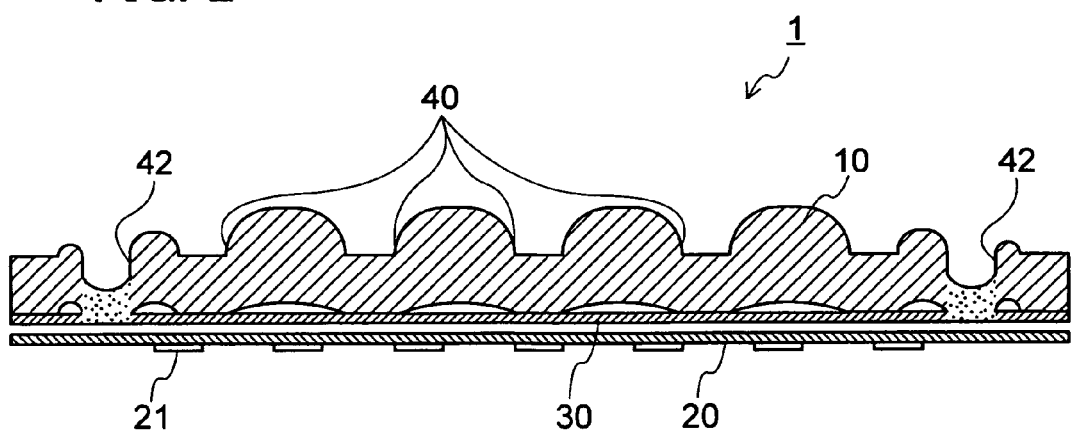
FIG. 2 shows the III-III line cross-section diagram.
Figure 3:
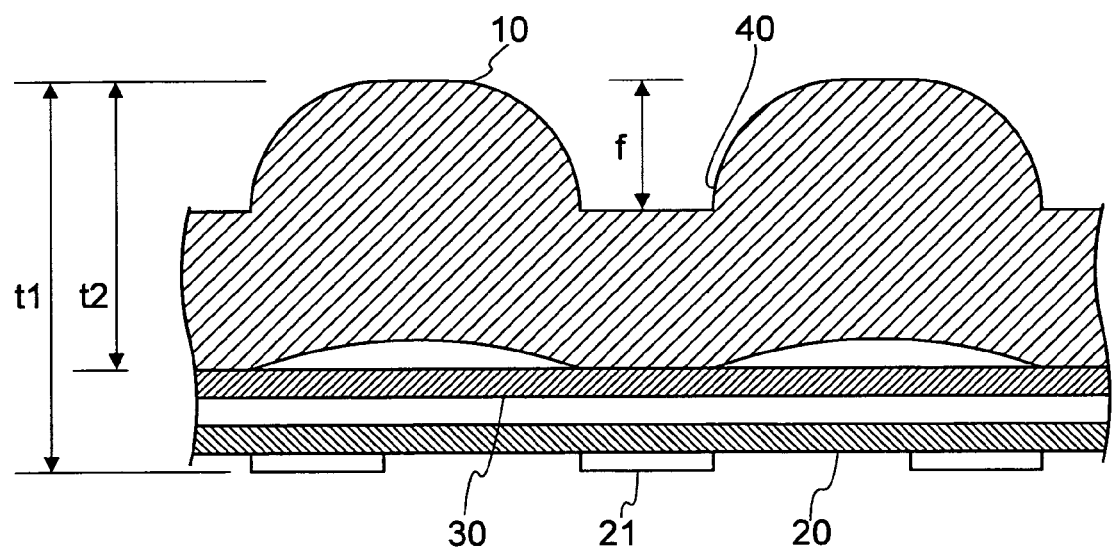
FIG. 3 shows the partially enlarged view of FIG. 2.

FIG. 1 shows the plan view to illustrate the skin side surface of the absorbent article, for example, a panty liner 1, according to one embodiment of the present invention. FIG. 2 shows the III-III line cross-section diagram of FIG. 1. FIG. 3 shows the partially enlarged view of FIG. 2.

In the two surfaces, which are elements of which the absorbent article consists, the surface facing to a wearer's body is hereinafter referred to as "skin side surface", and the opposite surface is hereinafter referred to as "garment side surface". Unless the size of each element is specified in particular, the size determined in a lengthwise orientation, for example, Oy-Oy along the line illustrated in FIG. 1, is referred to as "longitudinal size", and the size determined in a widthwise orientation, for example, III-III along the line illustrated in FIG. 1, is referred to as "latitudinal size".

The panty liner 1 provides a liquid permeable top sheet 10, a liquid impermeable back sheet 20, and an absorbent body 30 having liquid maintenance.

The plurality of concave portions are formed of the embossed compressed portions 40 on the top sheet 10. The top sheet 10 and the absorbent body 30 are joined through the embossed compressed portions 40.

In addition, to prevent the decomposition of the panty liner 1 in use, the top sheet 10 and the absorbent body 30 are joined through the junction portion 42 provided around the periphery of the panty liner 1. This junction portion 42 is formed by the well-known means, such as heat sealing, and ultrasonic sealing. The junction portion 42 may be provided at the most is preferable at the most peripheral region of the panty liner 1. In addition, the junction portion 42 may be disposed toward the inside from the most peripheral region. In this case, the distance from the most peripheral region may not be equal.

The back sheet 20 and the absorbent body 30 are joined by means, such as adhesive, for example, heat adhesive, adhesive tape, heat emboss, or ultrasonic emboss.

In addition, on the garment side surface on the back sheet 20, a pressure sensitive adhesive layer 21 is provided to fix the panty liner 1 to the underwear. For example, the amount of the applied pressure sensitive adhesive is 35 g/m².

Form and Size

The panty liner 1 is in approximately rectangular form having a front peripheral region 2 with a curved shape and a rear peripheral region 3 with a similar curved. For example, the longitudinal size along the center line Oy is 140 mm, and the latitudinal size is from 44 mm to 54.5 mm.

The absorbent body 30 is also in approximately rectangular form, having a front peripheral region with a curved shape and a rear peripheral region with a similar curved. The front peripheral region and the rear peripheral region of the absorbent body 30 are located slightly inside of the front peripheral region 2 and the rear peripheral region 3 of the panty liner 1. Right and left both side end portions of absorbent body 30 are in form of generally rectilinear figure that is parallel to longitudinal center line Oy. The size of the absorbent body 30 is nearly the same as that of the panty liner 1, provided around the center of the panty liner 1.

In addition, the absorbent body 30 is in approximately rectangular without any limitation, and may be in sheet form, fabric form, and the like.

The pressure sensitive adhesive layer 21 is formed in both of the right and left sides along the longitudinal centerline Oy approximately parallel to the longitudinal centerline Oy by longitudinal center. For example, nine pressure sensitive adhesive layers, of which the longitudinal size is 115 mm and the latitudinal size is 2 mm, are provided every 2.5 mm, defining longitudinal centerline as a symmetry axis.

Top Sheet

The top sheet 10 is liquid permeable, and typically, hydrophilic. In addition, the top sheet 10 is contact with the skin of the wearer, so that materials having superior flexibility and texture are preferably used. Specifically, nonwoven fabric processed from chemical fiber, synthetic fiber, and natural fiber by way of appropriate means, such as through-air, spunlace, spunbond, thermal bond, melt blown, and needle punch; and liquid permeable consisting of synthetic resin, such as polypropylene, are used for the top sheet 10. In addition, the top sheet 10 is preferably formed by overlaying plural sheets of these nonwoven fabrics to improve the feeling and bulkiness. The feel to the touch and the bulkiness of the top sheet 10 can be improved by applying a heat treatment, or increasing the weight.

For example, the top sheet 10 is formed by laminating a first layer and a second layer. The first layer is formed by a core-in-sheath composite synthetic fiber with a core of polyethylene terephthalate (PET) resin, and a sheath of polyethylene (PE) (fiber diameter: 2.2 dtex, fiber length: 45 mm). The second layer is formed by a core-in-sheath composite synthetic fiber with a core of polyethylene terephthalate (PET) resin, and a sheath of polyethylene (PE) (fiber diameter: 2.2 dtex, fiber length: 45 mm), and the first layer is formed by a core-in-sheath composite synthetic fiber with a core of polyethylene (PE) resin, and a sheath of polypropylene (PP) (fiber diameter: 2.2 dtex, fiber length: 45 mm). This structure is formed by fibrillating with a card, lying in web form, and forming by applying a hot air treatment. The weight of the first layer is from 7 g/m² to 93 g/m², for example, 20 g/m². The weight of the second layer is from 7 g/m² to 93 g/m², for example, 15 g/m². The weight of the entire top sheet 10 is from 14 g/m² to 100 g/m², for example, 35 g/m².

The top sheet 10 is not limited to two layer structure, and may be a single layer structure, and three or more layer structure. However, one nonwoven fabric is used for the top sheet 10 in each structure.

Back Sheet

The back sheet 20 is typically air impermeable, or air permeable but liquid impermeable. Specifically, the back sheet 20 is formed by a high water resistant nonwoven fabric, such as a nonwoven fabric, in which a plastic film, such as polypropylene, polyethylene, polyethylene terephthalate, ethylene vinyl acetate, or in combination thereof, and a resin film are adhered, a laminate material, in which nonwoven fabric is laminated on a plastic film, and an SMS (span bond-melt blown-span bond) nonwoven fabric, of which main material is polypropylene, or SMS/MB(melt blown)/SMS nonwoven fabric.

For example, the back sheet 20 is an air impermeably plastic film consisting of polypropylene and the weight is from 15 g/m² to 60 g/m², for example, 23 g/m².

Absorbent Body

Typically, the absorbent body 30 is preferably liquid absorbing ability, and liquid maintenance. The absorbent body 30 consists of. materials, in which the liquid permeable paper or cellulose sheet wraps grinded pulp, polymer having high absorbing ability is mixed, or the like. Specifically, a file consisting of a nonwoven fabric, in which chemical fiber, synthesized fiber, and natural fiber, and the like are processed by appropriate means, such as span lace, span bond, and needle punch, and the like, and a synthetic resin, such as polyethylene. In addition, the absorbent body 30 may have a structure, in which plural sheets of these non-wave fabrics are laid.

In addition, the absorbent body 30 is preferably included 50% or more of cellulosic fiber to improve the absorbing ability and maintenance of body fluid. This cellulosic fiber includes cotton fiber, rayon fiber, pulp fiber, and the like.

For example, the absorbent body 30 is a nonwoven fabric produced by mixing rayon fiber and polyethylene terephthalate fiber in the ratio of rayon:polyethylene terephthalate=9:1, and applying span lace. The weight is from 18 g/m² to 50 g/m², for example, 25 g/m².

Concave Portion

The concave portion is formed of the embossed compressed portions 40 with an adhesive, adhesive tape, heat emboss, or ultrasonic emboss, or in combination thereof.

In the present embodiment, the concave portions, which are formed of the embossed compressed portions 40 in rectangular like shapes, are respectively disposed in chessboard pattern without any limitations. For example, the concave positions may be dispersed or arranged in dispersion disseminated in a single line or plural straight lines, curved lines (e.g. wave patterns), a reticular patterns and zigzag lines. Then the concave positions are dispersed, each of them may have any shapes, such as a round, triangle, and quadrangle.

Pressure Sensitive Adhesive Layer

The pressure sensitive adhesive layer 21 may consist of rubber hot melt adhesive, olefinic hot melt adhesive, mechanical fastener, styrene brace material, and the like. In addition, the pressure sensitive adhesive layer 21 is covered with a released paper on which mold lubricant are treated.

Apparent Thickness

The term "apparent thickness" used herein indicates sectional thickness photographed under no load. The apparent thickness (t1) of a panty liner 1 is 0.5 mm to 5.0 mm (for example, 1.49 mm). The apparent thickness (t2) of a panty liner 1 is 0.35 mm to 5.0 mm (for example, 1.30 mm). As a result, t2 is 70% to 100% to t1.

The distance between the skin contact surface at the region on which the concave portions formed of the embossed compressed portions 40 are provided and the absorbent body 30 is 5% to 50% to that of between the region on which no concave portions are provided, and the absorbent body 30. In other words, the depth of the concave portion, showed as "f" in the FIG. 3, is 50% to 95% to t2.

For example, the apparent thickness of a region without concave portions formed is 1.5 mm, and the apparent thickness of a region with concave portions formed is 0.5 mm. In other words, t2 is 1.5 mm, and the depth of the embossed compressed portions 40 is 1.0 mm.

Here, the apparent depth of the panty liner 1 and the top sheet 10 are determined as follows. First, a 30 mm×30 mm test piece is cut off from the panty liner 1. Second, an approximately parallel cut surface is prepared in the longitudinal direction, and then, the microphotograph of the cut surface is taken with a stereoscopic microscope ("SZH10", by OLYMPUS CORPORATION). From the microphotographs, the maximum thickness of the panty liner 1 is determined as the apparent thickness of the panty liner 1. Third, at the portion measuring the maximum thickness of this panty liner 1, the thickness of the top sheet 10 is determined as the apparent thickness of the top sheet 10 (t2).

Klemm Capillary Rise Height

The capillary rise height (h2) of the absorbent body is higher than the capillary rise height (h1) of the top sheet. The h2 is preferably more than 2 times (e.g. 7.7 times in the fiber orientation, and 6.4 times in the orientation orthogonal to the fiber orientation) as high as h1.

The method for forming in this way is not limited; however, for example, the density of the absorbent body 30 is increased more than that of the top sheet 10, to make a difference between the capillary action of the absorbent and the top sheet. In addition, hydrophilic oil is applied to the fiber of the absorbent body 30, or cellulosic fiber is mixed to the absorbent body 30 as many as possible, to relatively increase the hydrophilic degree of the absorbent body 30, as well as h2.

For maintaining the lubricating characteristic of the liquid transferred, even at the region around the concave portions formed of the embossed compressed portions 40, on which the bulk is decreased, the Klemm capillary rise height of the top sheet 10 is preferably higher than that of the absorbent body 30.

The Klemm capillary rise heights of the top sheet 10 and the absorbent body are determined based on JIS P8141. The test is performed in the ambient air (20 degrees C., 65% RH) corresponding to the condition of JIS P8141. Distilled water is put in a container, and the temperature of the water is 15 degrees C. to 20 degrees C. First, 120 mm×15 mm test pieces are cut off from the top sheet 10 and the absorbent body 30. Parallel bench marks are lined at 5 mm away from the short sides of these test pieces, and then the test pieces are dipped in the water down to the bench marks and vertically maintained for 10 minutes. Then, the height that water rises from the bench mark is read at the middle of the width of the test piece as Klemm capillary rise height. In addition, in view of that the subject is nonwoven fabric, Klemm capillary rise heights are respectively determined in the fiber orientation, and the orientation orthogonal to the fiber orientation, to calculate the mean value for each of the directions.

Density

As described above, the density of the absorbent body 30 is increased more than that of the top sheet 10, so that the capillary rise height (h2) of the absorbent body is higher than the capillary rise height (h1) of the top sheet. For example, the density (d1) of the top sheet 10 is 0.0125 g/cm³ to 0.150 g/cm³, for example, 0.027 g/cm³, and the density (d2) of the absorbent body 30 is 0.05 g/cm³ to 0.25 g/cm³, for example, 0.16 g/cm³.

The density of the top sheet 10 is determined as follows. First, a 30 mm×30 mm test piece is cut off from the top sheet 1. An approximately parallel cut surface is prepared in the longitudinal direction, for example, the fiber orientation (i.e. the flow direction on the nonwoven fabric production), of this test piece. From this cut surface, the apparent thickness (t2) of the top sheet 10 is determined as well as the abovementioned apparent thickness. Second, from the area (a1×b1) of the top sheet 10 determined before the top sheet 10 and the absorbent body 30 are joined and shrunk, the area (a2×b2) of the top sheet 10 determined after the top sheet shrinks when the top sheet 10 and the absorbent body 30 are joined, and the shrinking area rate A (%) is calculated by using the formula, shrinking area rate A=((a1×b1−a2×b2)÷(a1×b1))×100. From this shrinking area rate A (%), and the weight of the top sheet 10 determined before the top sheet 10 shrinks when the top sheet 10 and the absorbent body 30, the weight (P2) of the top sheet 10 is calculated by using the formula, weight (P2) (g/m$^2$)=P1×100/(100−A). Third, the density (d1) of the top sheet 10 is calculated by using the formula, d1 (g/cm$^3$)=P2× (1/1000)×(1/t1). The density d2 of the absorbent body is calculated as well as that of the top sheet 10.

According to the present embodiment, the following effect is provided.

(A) The apparent thickness (t2) of the top sheet 10 is at least 70% to the apparent thickness (t1) of the panty liner 1. Therefore, the skin contact surface and the absorbent body 30 are sufficiently segregated, so that increasing moisture at the skin contact caused by the absorbent body 30 absorbing body fluid can be controlled. In addition, the top sheet 10 is provided well enough to reduce or disperse the pressure from the wearer to the absorbent body 30, so that reversing body fluid absorbed in the absorbent body 30 toward the skin side can be controlled.

(B) The apparent thickness (t2) of the top sheet 10 is no more than 95% to the apparent thickness (t1) of the panty liner 1. Therefore, the absorbent body 30, the back sheet 20, and the like can be provided well enough to sufficiently absorb body fluid and to inhibit body fluid seepage into the garment side.

(C) The absorbent body 30 consists of the structure, in which the capillary rise height (h2) is higher than the capillary rise height (h1) of the top sheet 10. Therefore, body fluid, which is discharged into the top sheet, is absorbed into the absorbent body 30 to control body fluid remaining at the skin contact surface, which causes discomfort for the wearer. In addition, since body fluid which was drawn into the absorbent body 30 is held inside the absorbent body 30, more body fluid can be absorbed and held.

(D) The apparent thickness (t1) of the panty liner 1 is 0.5 mm or more, so that these components can be provided well enough to sufficiently absorb body fluid. In addition, t1 is 5 mm or less to reduce feelings of discomfort for the wearer. Therefore, the panty liner 1 is preferably used as a thinner absorbent article.

(E) The top sheet 10 provides a plurality of embossed compressed portions, and through the portion of the skin surface of the top sheet in contact with the absorbent body 30, body fluid discharged is quickly transferred into the absorbent body 30 thereby to quickly control body fluid remaining at the skin contact surface, which causes discomfort for the wearer.

(F) The depth of the concave portions formed by the embossed compressed portions 40 are at least 50% to the apparent thickness (t2) of the top sheet 10, so that the skin side surface of the top sheet 10 and the absorbent body 30 become closer at the concave portion. Therefore, through these concave portions, discharged body fluid is quickly transferred into the absorbent body, to quickly control body fluid remaining at the skin contact surface, causes discomfort for the wearer.

(G) The depth of the embossed compressed portions 40 is no more than 95% to the apparent thickness (t2) of the top sheet 10, so that the thickness of the top sheet 10 on which the embossed compressed portions are provided is sufficiently formed. Thus, through these regions, body fluid absorbed in the absorbent body reversed toward the skin side through the region can be controlled.

(H) The concave portions are formed of the embossed compressed portions 40. A relatively high density region is formed at the region of the top sheet 10, at which the embossed compressed potions 40 are disposed. Discharged body fluid is absorbed into the embossed compressed portions 40, which is a high density region, by way of capillary action based on density gradient. Thus, body fluid is quickly transferred into the absorbent body 30, to quickly control body fluid remaining at the skin contact surface, which causes discomfort for the wearer.

(I) The absorbent body 30 includes fiber on which hydrophilic oil is applied. The hydrophilicity degree of the absorbent body 30 can be relatively higher than that of the top sheet 10. Thus, body fluid is quickly transferred into the absorbent body, to quickly control body fluid remaining at the skin contact surface, which causes discomfort for the wearer.

(J) The absorbent body 30 includes cellulosic fiber. The hydrophilicity degree of the absorbent body 30 can be relatively higher than that of the top sheet 10. Thus, body fluid is quickly transferred into the absorbent body 30, to quickly control body fluid remaining at the skin contact surface, which causes discomfort for the wearer.

(K) The density of the absorbent body 30 is higher than that of the top sheet, so that discharged body fluid is absorbed into the absorbent body 30, by way of capillary action based on density gradient. Thus, body fluid is quickly transferred into the absorbent body 30, to quickly control body fluid remaining at the skin contact surface, which causes discomfort for the wearer.

(L) The density of the absorbent body is 0.05 g/cm$^3$ or more, so that the density of the absorbent body is higher than that of the density of the top sheet. Thus, body fluid is quickly transferred into the absorbent body 30, to quickly control body fluid remaining at the skin contact surface, which causes discomfort for the wearer. Alternatively, the density of the absorbent body 30 is 0.25 g/cm$^3$ or less so as to absorb and maintain much more body fluid.

(M) The density of the top sheet 10 is 0.0125 g/cm$^3$ or more to sufficiently form the top sheet 10. The absorbent article has a soft touch for the wearer. The density of the top sheet 10 is 0.150 g/cm$^3$ or less, so that body fluid is absorbent into the top sheet 10 to quickly control body fluid remaining at the skin contact surface, which causes discomfort for the wearer.

Moreover, the present invention is not limited to the above described embodiments, and includes modification, improvement, or the like in the scope of the object to achieve the present invention. For example, the shapes of the panty liner 1 may include a round, rectangle, bone, oval, and the like.

EXAMPLES

Example 1

Top Sheet

The first layer that was formed by a core-in-sheath composite synthetic fiber with a core of polyethylene terephthalate (PET) resin and a sheath of polyethylene (PE) (fiber diameter: 2.2 dtex, fiber length: 45 mm), and the second layer that was formed by a core-in-sheath composite synthetic fiber with a core of polyethylene terephthalate (PET) resin and a sheath of polyethylene (PE) (fiber diameter: 2.2 dtex, fiber length: 45 mm) and a core-in-sheath composite synthetic fiber with a core of polyethylene (PE) resin and a sheath of polypropylene (PP) (fiber diameter: 2.2 dtex, fiber length: 45 mm) were fibrillated with a card, laid in web form, and then a hot air treatment was applied on the layers to form a bilayer structure. The weight of the first layer was 20 g m$^2$, which of the second layer was 15 g/m$^2$, and that of the entire top sheet 10 was 35 g/m$^2$.

Back Sheet

An air impermeable plastic film consisting of polypropylene having the weight of 23 g/m² was applied as a back sheet.

Absorbent Body

A nonwoven fabric was produced by mixing rayon fiber and polyethylene terephthalate fiber in the ratio of rayon:polyethylene terephthalate=9:1, and by way of span lace, and then 25 g/m² of the obtained nonwoven fabric was applied as an absorbent body.

Preparation of Panty Liner

The top sheet and the absorbent body of the abovementioned materials were laid in order from the skin side, and then partially joined with a heat adhesive. By pressing with an embossing plate on which 3 mm high rectangular pins provided in the shape of chessboard patterns, plural concave portions were formed of 1.00 mm deep embossed compressive portions. Then, the back sheet was disposed on the side to which the top sheet of the absorbent was not joined, to prepare a panty liner by partially joining with a heat adhesive.

In this Example, 3 mm high rectangular pins were used for the embossing plate; however, any pins higher than the thickness of the conjugate of the top sheet and the absorbent body may be used, and the height of the pin may usually be in the range of 0.6 mm to 5.5 mm.

Comparative Examples 1 to 5

The panty liner was prepared with the same materials used in Example, in the same way of Example, except that the thickness of each of the materials was changed, and the embossed compressed portions were not provided. What changed is shown in Table 1.

Measurement of Klemm Capillary Rise Height

The Klemm capillary rise height was measured in the ambient air (20 degrees C., 65% RH) corresponding to the condition of JIS P8141. Distilled water was put in a container, adjusting water at 18 degrees C. First, 120 mm×15 mm test pieces were cut off from the top sheet and the absorbent body of the panty liner prepared in Example and Comparative Examples 1 to 5. Parallel bench marks were Lind at 5 mm away from the short sides of these test pieces, and then the test pieces were dipped in the water down to the bench marks and vertically maintained for 10 minutes. Then, the height that water rose from the bench mark was read at the middle of the width of the test piece as Klemm capillary rise height. In consideration of that a subject is nonwoven fabric, the Klemm capillary rise heights were respectively determined in the fiber orientation, and the orientation orthogonal to the fiber orientation, to calculate the mean value for each of the directions. This result is shown in Table 1.

Evaluation of Surface Characteristics

The softness to the skin contact surface regarding the panty liners prepared in Example and Comparative Examples 1 to 5 was evaluated. Of 17 woman trials, the number of the trials, who evaluated that the surface of the panty liner was soft, which means the surface characteristics was superior, is shown Table 1.

Evaluation of Absorbing Ability

The menstrual blood concealment, whether or not menstrual blood remained at the skin contact surface, regarding the panty liners prepared in Example and Comparative Examples 1 to 5 was evaluated. Of 17 woman trials, the number of the trials, who evaluated that the menstrual blood concealment, i.e. absorbing ability, was superior, is shown Table 1.

TABLE 1

| | | Example 1 Non Embossed Portion | Example 1 Embossed Portion | Comparative Examples 1 | 2 | 3 | 4 | 5 |
|---|---|---|---|---|---|---|---|---|
| Apparent Thickness (mm) | Entire | 1.49 | 0.71 | 1.66 | 1.73 | 1.81 | 1.93 | 1.42 |
| | Top Sheet | 1.30 | 0.49 | 0.32 | 0.31 | 1.23 | 0.36 | 0.39 |
| | Absorbent body | 0.15 | 0.17 | 1.29 | 1.36 | 0.52 | 1.52 | 0.97 |
| | Back Sheet | 0.05 | 0.04 | 0.05 | 0.05 | 0.06 | 0.05 | 0.06 |
| Klemm Capillary Rise Height (mm) | Top Sheet Orthogonal Orientation to Fiber Orientation | 9 | | 70 | — | 7 | 8 | 8 |
| | Fiber Orientation | 8 | | — | 98 | — | — | — |
| | Absorbent body Orthogonal Orientation to Fiber Orientation | 80 | | 8 | — | 44 | 43 | 31 |
| | Fiber Orientation | 51 | | — | 7 | — | — | — |
| Top Sheet/Entire (%) | | 87.2 | 69.0 | 19.3 | 17.9 | 68.0 | 18.7 | 27.5 |
| Top Sheet/Absorbent body (%) | | 11.5 | 34.7 | 403.1 | 438.7 | 42.3 | 422.2 | 248.7 |
| Evaluation of Surface Characteristics | | 17 | | 2 | 5 | 14 | 2 | 8 |
| Evaluation of Absorbing Ability | | 17 | | 0 | 0 | 6 | 4 | 9 |

As shown in table 1, in the panty liner prepared in Example, the apparent thickness of the top sheet was 87.0% to that of the entire panty liner, in other words, 70% to 95%, and the capillary rise height of the absorbent body is higher than that of the top sheet.

In addition, for the panty liner prepared in Example, all 17 trials evaluated that the absorbing ability was superior. In contrast, for the panty liners prepared in Comparative Examples, 2 to 14 trials merely evaluated that the surface characteristics was superior.

In addition, for the panty liner prepared in Example, all 17 trials evaluated that the surface of the panty liner was soft. In contrast, for the panty liners prepared in Comparative Examples, 2 to 14 trials merely evaluated that the surface characteristics was superior.

As the abovementioned result, the panty liner of the present invention exhibits the soft skin contact surface and less impact to the skin, superior surface characteristics enabling to obtain soft touch with rich cushioning characteristics, and superior absorbing ability quickly transferring discharged body fluid into the absorbent body.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article comprising:
a liquid permeable top sheet;
a liquid impermeable back sheet; and
an absorbent body disposed between the top sheet and the back sheet, the top sheet and the absorbent body are joined through embossed compression portions, said absorbent body being in direct contact with the back sheet at least in a central portion of the absorbent article,
wherein an apparent thickness, which is a sectional thickness under no load, of the top sheet is 70% to 95% of an apparent thickness which is a sectional thickness under no load, of the absorbent article, and
a Klemm capillary rise height of the absorbent body is higher than a Klemm capillary rise height of the top sheet,
wherein the apparent thickness of the absorbent article is from 0.5 mm to 5 mm.

2. The absorbent article according to claim 1, wherein the top sheet provides a plurality of concave portions.

3. The absorbent article according to claim 2, wherein a depth of the concave portions is from 50% to 95% the apparent thickness of the top sheet.

4. The absorbent article according to claim 2, wherein the concave portions are formed of the embossed compressed portions.

5. The absorbent article according to claim 1, wherein the absorbent body includes fiber on which hydrophilic oil is applied.

6. The absorbent article according to claim 1, wherein the absorbent body includes cellulosic fiber.

7. The absorbent article according to claim 1, wherein the density of the absorbent body is higher than that of the top sheet.

8. The absorbent article according to claim 7, wherein the density of the absorbent body is from 0.05 $g/cm^3$ to 0.25 $g/cm^3$.

9. The absorbent article according to claim 7, wherein the density of the absorbent body is from 0.125 $g/cm^3$ to 0.150 $g/cm^3$.

* * * * *